United States Patent
Choi et al.

(10) Patent No.: US 12,427,100 B2
(45) Date of Patent: Sep. 30, 2025

(54) TOPICAL COMPOSITION COMPRISING RETINOL AND PDRN AND USE OF SAME

(71) Applicants: DR. J SKINCLINIC, INC., Cerritos, CA (US); PHARMARESEARCH CO., LTD., Gangneung-si (KR)

(72) Inventors: Youngmin Choi, Cerritos, CA (US); Sung Eun Lee, Gangneung-si (KR); Jonghwan Kim, Gangneung-si (KR); Sujong Kim, Yongin-si (KR)

(73) Assignees: DR. J SKINCLINIC, INC., Cerritos, CA (US); PHARMARESEARCH CO., LTD., Gangneung-si (KR)

( * ) Notice: Subject to any disclaimer, the term of this patent is extended or adjusted under 35 U.S.C. 154(b) by 680 days.

(21) Appl. No.: 17/865,156

(22) Filed: Jul. 14, 2022

(65) Prior Publication Data
US 2023/0140298 A1      May 4, 2023

Related U.S. Application Data

(60) Provisional application No. 63/292,797, filed on Dec. 22, 2021, provisional application No. 63/273,089, filed on Oct. 28, 2021.

(51) Int. Cl.
| | | |
|---|---|---|
| *A61K 8/67* | (2006.01) | |
| *A61K 8/60* | (2006.01) | |
| *A61Q 19/02* | (2006.01) | |
| *A61Q 19/08* | (2006.01) | |

(52) U.S. Cl.
CPC .............. *A61K 8/671* (2013.01); *A61K 8/606* (2013.01); *A61Q 19/02* (2013.01); *A61Q 19/08* (2013.01); *A61K 2800/75* (2013.01)

(58) Field of Classification Search
CPC .. A61K 8/606; A61K 8/671; A61K 2800/592; A61K 2800/75; A61Q 19/00; A61Q 19/02; A61Q 19/08
See application file for complete search history.

(56) References Cited

U.S. PATENT DOCUMENTS

2011/0020414 A1    1/2011    Kunin

FOREIGN PATENT DOCUMENTS

| CN | 113332162 A   | 9/2021 |
| JP | 2011207849 A  | 10/2011 |
| KR | 20100092925 A | 8/2010 |
| WO | 2018008873 A1 | 1/2018 |

OTHER PUBLICATIONS

Rejuran Advanced Anti-Aging Retinol + c-PDRN Serum, Jan. 22, 2021 Instagram post (downloaded from https://www.instagram.com/p/CKWu55THNEg/ on Jul. 7, 2025).*

(Continued)

*Primary Examiner* — Terra C Gibbs
(74) *Attorney, Agent, or Firm* — Nixon Peabody LLP

(57) ABSTRACT

Skin care compositions and methods are provided. In some embodiments, the skin care compositions include retinol and polydeoxyribonucleotide (PDRN). In certain embodiments, methods of using the aforementioned skin care compositions are provided as treatment for skin aging and/or acne scars.

15 Claims, 7 Drawing Sheets

(56) References Cited

OTHER PUBLICATIONS

Rejuran—What is c-PDRN & why do I want to pair it with Retinol? Mar. 6, 2021 Instagram post downloaded from https://www.instagram.com/p/CMFX2M9nh7y/?hl=en on Jul. 7, 2025).*
Azyre, Advanced Anti-aging C-pdm® + Retinol Serum, INCIDecoder, Jan. 26, 2022 [retrieved on Nov. 30, 2022]. Retrieved from the Internet:<URL:https://incidecoder.com/products/rejuran-advanced-anti-aging-c-pdrn-r-retinol-serum>, entire document.
ISR and WO for PCT/US2022/078512 mailed Jan. 6, 2023, 8 pages.
Korean Office Action for KR 10-2024-7017689 dated Aug. 1, 2024, 19 pages.
Barrell, Can retinol help treat acne?, MedicalNews Today, May 18, 2021, 6 pages.
Draelos, Updates in medial skin care, Advances in Cosmetic Surgery, 2018 1:211-217, 7 pages.
Fife, Practical evaluation and management of atrophic acne scars, Tips for the General Dermatologist, Journal of Clinical and Aesthetic Dermatology, 2011, 4(8):50-57, 8 pages.
Mayo Clinic, Wrinkles, Mar. 5, 2021, http://web.archive.org/web/20210305044004/https://www.mayoclinic.org/diseases-conditions/wrinkles/diagnosis-treatment/drc-20354931, 4 pages.
Tan et al., The role of topical retinoids in prevention and treatment of atrophic acne scarring: understanding the importance of early effective treatment, J. Drugs Dermatol. 2019, 18(3):255-260, 4 pages.

* cited by examiner

- C: Control
- NC: Negative control
- PC1: Positive control1, Quercetin[μg/mL]
- PC2: Positive control2, 18β-Glycyrrhetinic acid[μM]

Before — After 4 weeks

Before — After 4 weeks

Before — After 4 weeks

TOPICAL COMPOSITION COMPRISING RETINOL AND PDRN AND USE OF SAME

CROSS-REFERENCE TO RELATED APPLICATIONS

This application includes a claim of priority under 35 U.S.C. § 119(e) to U.S. provisional patent application Nos. 63/273,089, filed Oct. 28, 2021 and 63/292,797, filed Dec. 22, 2021, the entirety of which is hereby incorporated by reference.

FIELD OF INVENTION

The instant disclosure relates to compositions and methods for skin care. The instant disclosure provides compositions including retinol (vitamin A1-alcohol) and polydeoxyribonucleotide (PDRN), and methods of treating skin by topically applying the composition to skin of a subject.

BACKGROUND

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Both retinol and PDRN are widely used for their effects on skin. Nevertheless, no topical compositions including both retinol and PDRN are known.

Retinol, which is a type of retinoid, is a form of vitamin A. In recent years, retinol has gained popularity in the skin care market, due to its anti-aging effects. Retinol is used in a variety of cosmetic products for topical application. For example, retinol is used to fade the look of wrinkles in skin, smooth fine lines, improve skin texture, and brighten skin tone.

Over-the-counter retinol comes in doses of up to 2%, according to the American Academy of Dermatology (AAD). Stronger retinol may require a prescription. A person will typically use retinol as a topical treatment or apply it to skin. Retinol is known to reduce inflammation by blocking molecules that can cause inflammation. Retinol is also known to protect against the breakdown of collagen, and it stimulates cell turnover and collagen production in the skin.

Despite the above described benefits, some side effects of retinol are known. Common side effects of retinol include itchy, dry, and flushed skin. Further, retinol is known to induce mild erythema on the skin. It is not clear whether the redness induced by retinoid is caused by the sensitization or irritation. A lot of people feel that their skin is very sensitive and experience peeling, flaking, and irritation after applying retinol to their skin. Retinol side effects will typically occur when a person uses retinol for a prolonged period of time or uses a higher concentration. According to a study, signaling mediators of retinol-induced irritation are proinflammatory cytokines such as IL-8(interleukin-8) and MCP-1(monocyte chemoattractant protein-1). See "The mechanism of retinol-induced irritation and its application to anti-irritant development" in Toxicology Letters 146 (2003) 65-73: Bae-Hwan Kim 1, Yong-Soon Lee, Kyung-Sun Kang. There is clearly a need in the art for skin care compositions/formulations including retinol that improve the condition of skin without irritating skin.

PDRN is a mixture of deoxyribonucleotides with molecular weights varying from 50 to 1500 kDa derived from gonads or sperm cells of *Oncorhynchus mykiss* (salmon trout) or *Oncorhynchus keta* (Chum Salmon). PDRN is known to have many positive therapeutic effects such as improving angiogenesis, promoting osteoblast activity, increasing collagen synthesis, and an anti-inflammatory effect.

Scientific studies have shown that PDRN is an agonist of adenosine A2a receptor. In particular, PDRN has anti-inflammatory effects, increases cell growth, and improves microcirculation by stimulating A2 receptor. PDRN also plays a role in DNA synthesis via nucleotide salvage pathways. PDRN has been shown to be effective in tissue regeneration and wound healing by promoting fibroblast proliferation and extra cellular matrix.

PDRN has been used in the medical community, especially in dermatology, as an injectable composition for tissue regeneration to accelerate the natural wound healing process in the body. For example, Jeong et al. studied anti-inflammatory effects of PDRN on scar formation and found that PDRN exerts anti-inflammatory and collagen synthesis effects via HMGB-1 suppression, preventing scar formation. (Jeong W, Yang C E, Roh T S, Kim J H, Lee J H, Lee W J. Scar Prevention and Enhanced Wound Healing Induced by Polydeoxyribonucleotide in a Rat Incisional Wound-Healing Model. Int J Mol Sci. 2017 Aug. 3; 18(8):1698.) In general, PDRN is administered to a wound area of a subject via intraperitoneal or subcutaneous injection as described in Jeong et al., Shin et al. (Shin, D. Y., Park, J U., Choi, M H. et al. Polydeoxyribonucleotide-delivering therapeutic hydrogel for diabetic wound healing. Sci Rep 10, 16811 (2020).), and U.S. Pat. No. 10,456,347.

WO2018008873A1 discloses a cosmetic composition containing PDRN and, more specifically, to a PDRN-containing cosmetic composition which contains PDRN, glutathione and hyaluronic acid as major ingredients. Apparently, the cosmetic composition disclosed in WO2018008873A1 has effects of strengthening resilience from the basal layer of the skin, providing dewy hydration, and whitening. However, the cosmetic composition disclosed in WO2018008873A1 does not include retinol.

KR20100092925A discloses PDRN as a skin transformation ingredient. c-PDRN® manufactured by PharmaResearch (Seongnam-si, Gyeonggi-do, Korea) is a version of PDRN, a form of marine-based hydrolyzed DNA, that has been shown to reignite the repair process in skin. c-PDRN® is a marine growth factor (MGF) whose molecular size allows for greater effectiveness due to its penetrability. That is, c-PDRN® is small in size and capable of working with other active ingredients to optimize their performance. It has been shown that compositions including c-PDRN® helps improving the appearance of skin damaged by dark spots, acne scars, sun damage, hormonal fluctuations, and burn marks for smoother, healthier-looking skin, when combined with other active ingredients such as niacinamide and bisabolol. However, none of the known compositions including PDRN includes retinol.

As mentioned above, although the art provides topical uses for retinol and PDRN separately, no compositions including both retinol and PDRN are known. Inventors found that topical application of a combination of these two ingredients beneficially and synergistically boosts the activity of retinol and the activity of PDRN. This unexpectedly provides significant benefits for skin, including improving, reducing, inhibiting, or delaying the appearance of at least one sign of aging in skin, and reducing skin irritation that may be caused by individual ingredients. Accordingly, new compositions that improve the condition of skin and new methods of treating signs of skin aging are disclosed herewith. The new compositions provide antiaging properties among others, reducing the retinol side effects described above.

SUMMARY OF THE INVENTION

Various embodiments provide a composition for topical application to a subject's skin. In some embodiments, the composition includes retinol and polydeoxyribonucleotide (PDRN). In some aspects, a weight ratio of retinol to PDRN in the composition is in the range of about 1:1 to about 1:50, and in some aspects, the weight ratio of retinol to PDRN in the composition is in the range of about 1:5 to about 1:10.

In certain embodiments, an amount of retinol in the composition is in the range of about 0.01-about 1.00% w/w, and an amount of PDRN in the composition is in the range of about 0.01-about 5.00% w/w such that PDRN is effective as an anti-irritant in response to skin irritations causable by retinol applied to skin of a subject. In some embodiments, the composition further includes an excipient base in the range of about 94.00-about 99.98%. In certain embodiments, the amount of retinol in the composition is in the range of about 0.1-about 5% w/w; and the amount of PDRN in the composition is in the range of about 0.1-about 2.5% w/w. In certain embodiments, the amount of retinol in the composition is in the range of about 1-about 3% w/w; and the amount of PDRN in the composition is in the range of about 0.3-about 1.5% w/w or about 0.5-about 1% w/w.

In some aspects, the composition is a topical composition. In some aspects, the composition is a cosmetic, skin care, or anti-aging composition.

Various embodiments provide applying any of the compositions/formulations described above to a subject's skin. In some embodiments, the compositions are used to treat a sign of skin aging. In some embodiments, the region of the subject's skin to which the composition is applied includes one or more characteristics such as a lesion of acne, dryness, a lesion of psoriasis, a lesion of eczema, a lesion of dermatitis, a wrinkle, a lesion of cellulitis, or a combination thereof. In certain embodiments, the subject is a human. In some embodiments, one of the characteristics of the subject's skin is a lesion of acne. In some embodiments, one of the characteristics of the subject's skin is a lesion of psoriasis.

In some embodiments, a method for treating a sign of skin aging includes topically applying a composition comprising retinol and polydeoxyribonucleotide (PDRN) to skin in need of treatment for skin aging. In some embodiments, the method also includes identifying a subject in need of treatment for skin aging prior to applying the composition to the skin. In some aspects, the treating the sign of skin aging includes reducing fine lines and wrinkles on the skin. In some embodiments, the composition is applied to the skin 1-3 times a day. In some embodiments, the composition is applied to the skin for 1 week, 2 weeks, 3 weeks, or 4 weeks. In some embodiments, the composition is applied to the skin for 1 month, 2 months, 3 months, 4 months, or 5 months. In some embodiments, the composition is applied to the skin for at least 6 months. In some embodiments, the composition is applied to the skin for 1 year, 2 years, 3 years, 4 years, or 5 years. In some embodiments, the composition is applied to the skin indefinitely. In some embodiments, the composition is applied to the skin every 6-8 hours. In some aspects, the skin is facial skin.

In certain embodiments, the composition is topically applied to acne scars on the skin such that visibility of the acne scars disappears or is reduced. In some embodiments, a weight ratio of retinol to PDRN in the composition is in the range of about 1:1 to about 1:50 or about 1:5 to about 1:10. In certain embodiments, an amount of retinol in the composition is in the range of 0.01-1.00% w/w, and an amount of PDRN in the composition is in the range of 0.01-5.00% w/w such that the amount of PDRN is effective to treat, reduce or prevent skin irritations causable by retinol applied to skin of a subject. In some embodiments, the composition further includes an excipient base in the range of 94.00-99.98%.

In some embodiments, the amount of retinol in the composition is in the range of 0.1-5% w/w; and the amount of PDRN in the composition is in the range of 0.1-2.5% w/w. In certain embodiments, the amount of retinol in the composition is in the range of 1-3% w/w; and the amount of PDRN in the composition is in the range of 0.3-1.5% w/w or 0.5-1% w/w.

BRIEF DESCRIPTION OF THE FIGURES

Exemplary embodiments are illustrated in the referenced figures. It is intended that the embodiments and figures disclosed herein are to be considered illustrative rather than restrictive.

DETAILED DESCRIPTION OF THE INVENTION

Figure 1:
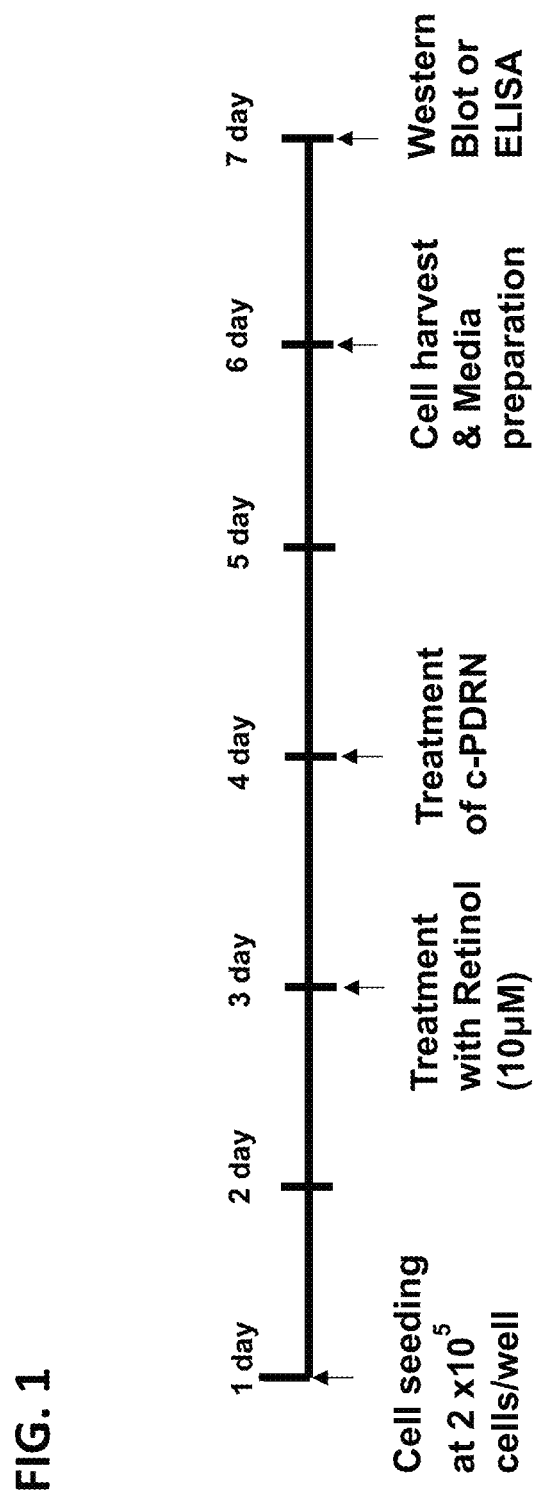
FIG. 1 shows a timeline for experiments performed to see effects of c-PDRN on retinol treated human skin cells.

Unless defined otherwise, technical and scientific terms used herein have the same meaning as commonly understood by one of ordinary skill in the art to which this invention belongs. Bolognia et al., *Dermatology* (2012); Barel et al., *Handbook of Cosmetic Science and Technology*, (2014); and Smith, *March's Advanced Organic Chemistry Reactions, Mechanisms and Structure* 7$^{th}$ ed., (2013); provide one skilled in the art with a general guide to many of the terms used in the present application.

Unless otherwise indicated, percentages used to express amounts of ingredients are percentage by weight (i.e., % (W/W). Similarly, weight ratios used to express relative proportions of ingredients are also determined using percentage by weight (i.e., weight ratios are calculated by dividing the percentage by weight of one ingredient by another). Unless stated otherwise, all ranges are inclusive of the endpoints, e.g., "from 1 to 10" includes the endpoints 1 and 10.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. Unless otherwise defined, all technical and scientific terms used herein have the same meaning as commonly understood by one of ordinary skill in the art to which this invention belongs. It should be understood that this invention is not limited to the particular methodology, protocols, and reagents, etc., described herein and as such can vary. The definitions and terminology used herein are provided to aid in describing particular embodiments, and are not intended to limit the claimed invention, because the scope of the invention is limited only by the claims.

As used herein the terms "composition(s)" and "formulation(s)" have the same meaning.

As used herein, "cosmetic" refers to a beautifying substance or preparation which preserves, restores, bestows, simulates, or enhances the appearance of bodily beauty or appears to enhance the beauty or youthfulness, specifically as it relates to the appearance of tissue or skin.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or skin condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

As used herein, "topically applying" means directly laying on or spreading on outer skin, the scalp, or hair, e.g., by use of the hands or an applicator such as a wipe, roller, or spray.

"Beneficial results" or "desired results" may include, but are in no way limited to, preventing or repairing damage to skin from any source (e.g., electromagnetic radiation, burns, scalds, acne, weather conditions, pathogens, genetic defect(s), physical trauma, chemical trauma, disease (e.g. diabetes) and combinations thereof), improving the softness of skin, improving the tone of skin, protecting and healing skin that has been recently tattooed, reducing the appearance of wrinkles in skin, and relieving dryness. With respect to disease conditions, beneficial results may include lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy.

"Diseases," "conditions" and "disease conditions," as used herein may include, but are in no way limited to skin diseases or conditions such as acne, cellulitis, skin dryness, eczema, atopic dermatitis, contact dermatitis, seborrheic dermatitis, cradle cap, nummular dermatitis, stasis dermatitis, perioral dermatitis (muzzle rash) dermatitis herpetiformis, echtima, folliculitis, impetigo, keratosis, actinic (solar) keratosis, keratosis pilaris, keratosis follicularis, hyperkeratosis, photoallergy, skin conditions associated with diabetes, psoriasis, HSV1 and HSV2, chicken pox, herpes zoster, measles, rubella, stress, tattoo removal, burns, scars, dark spots, depigmentation, vitiligo, combinations thereof and the like.

As used herein, the term "administering," refers to the placement of an agent, composition, or formulation as disclosed herein onto a subject by a method or route which results in at least partial localization of the agents or composition at a desired site. "Route of administration" may refer to any administration pathway known in the art, including but not limited to topical administration. Via the topical route, the agent or composition can be in the form of oil, skin scrub (i.e., formulation containing particulate matter that interacts with the skin), aerosol, droplet spray, lotion, cream, gel, ointment, suspensions, mousses, solutions or emulsions.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets. In particular embodiments, the subject is human.

A subject can be one who has been previously diagnosed with or identified as suffering from or having a condition in need of treatment (e.g., dry skin or any other condition described herein) or one or more complications related to the condition (e.g., psoriasis), and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. For example, a subject can be one who exhibits one or more symptoms for a condition or one or more complications related to the condition or a subject who does not exhibit symptoms. A "subject in need" of diagnosis or treatment for a particular condition can be a subject suspected of having that condition, diagnosed as having that condition, already treated or being treated for that condition, not treated for that condition, or at risk of developing that condition.

Retinol is a low-polarity functional ingredient primary soluble in the oil phase of emulsions, while PDRN is more polar, and soluble in the aqueous phase. Inventors evaluated anti-irritant activities of PDRN against retinol-induced irritation by measuring IL-8 and MCP-1 contents in the culture media of HaCaT cells treated with retinol. Inventors also conducted human study of anti-irritant efficacy against retinol-induced irritancy using patch test. Inventors found that a composition containing these ingredients is useful as an extraordinary anti-aging agent with synergistic, unexpected and extraordinary effects.

Skin Care Compositions

With the foregoing background in mind, in various embodiments, the invention teaches a skin care composition (also described herein as "formulation") that includes retinol and PDRN.

In some embodiments, the composition includes retinol in the range of 0.01-10%, 0.1-5%, or 1-3% w/w and PDRN in the range of 0.01-5.00%, 0.1-2.5%, 0.3-1.5%, or 0.5-1% w/w. In some embodiments, the ratio of retinol:PDRN in the composition is in the range of 1:1-1:50. In some embodiments, the ratio of retinol:PDRN in the composition is in the range of 1:5-1:10. Preferably, no prescriptions by doctors are required for the amounts of retinol and PDRN used in the composition.

In some embodiments, the composition further includes niacinamide that helps visibly improving the appearance of uneven skin pigmentation. In some embodiments, the composition further includes adenosine derived from yeast with skin-soothing and restoring properties to reduce the appearance of fine lines and wrinkles. In some embodiments, the composition further includes peptides, such as palmitoyl tripeptide-38 or palmitoyl tripeptide-5, that helps even skin tone to smooth the appearance of lines and wrinkles. In some embodiments, the composition further includes argan oil known to provide extreme hydration with high levels of Vitamin E and essential fatty acids. In some embodiments, the composition further includes bisabolol as a soothing agent to help brightening the appearance of skin. In some embodiments, the composition further includes ascorbic acid or Vitamin C that is highly effective antioxidant known to brighten skin tone and target signs of aging. In some embodiments, the composition further includes *Morus nigra* (mulberry) leaf extract as a source of polyphenol antioxidants to reverse visible hyperpigmentation. In some embodiments, the composition further includes *Salix albe* (willow bark) extract known for its soothing benefits for skin. In some embodiments, the composition further includes exfoliants such as lactic acid and/or salicylic acid. In some embodiments, the composition further includes an excipient base in the range of 94.00-99.98% w/w. The excipient base is a proven, functional, marketable skin care product in its own right.

Optionally, the composition including retinol and PDRN may further include the following ingredients. In some embodiments, the composition further includes *Allium cepa* (onion bulb) extract as an antioxidant-rich natural ingredient to help reducing the appearance of scars. In some embodiments, the composition further includes allantoin as a naturally-derived, antioxidant-rich ingredient for skin soothing and conditioning properties that help diminishing visibility of scars. In some embodiments, the composition further includes hyaluronic acid (sodium hyaluronate) that visibly plumps skin with moisture to reduce appearance of scars and pockmarks. In some embodiments, the composition further includes plant stem cells such as *Echinacea angustifolia* (cone flower) meristem cell culture to help strengthening skin. In some embodiments, the composition further includes *Rubus fruticosus* (blackberry) leaf extract as a potent antioxidant with high levels of Vitamin C to help fighting free radicals. In some embodiments, the composition further includes *Camellia sinensis* (black tea) leaf extract as an antioxidant for its skin soothing properties. In some embodiments, the composition further includes biotin to improve the appearance of uneven skin pigmentation. In some embodiments, the composition further includes pumpkin seed oil as a nourishing protectant rich in Vitamin E, zinc, omega 3- and 6-fatty acids, and antioxidants. In some embodiments, the composition further includes *Laminaria*

*dititata* (algae) extract to hydrate and protect skin and delicate hairs. In some embodiments, the composition further includes rice extract to condition and soften hairs, reducing potential for damages. In some embodiments, the composition further includes *Persea gratissima* (avocado) oil as a rich, nourishing moisturizer to help hairs look fuller and healthier. For example, the composition including retinol and PDRN may further include all or some of the above-identified ingredients.

The composition comprising retinol and PDRN may be made into a wide variety of product types that include but are not limited to serums, lotions, creams, gels, sticks, sprays, ointments, shampoos and hair conditioners, hair fixers, pastes, foams, patches, hydrogels, facial masks and skin masks, and films. These product types may contain several types of cosmetically acceptable topical carriers including, but not limited to solutions, suspensions, emulsions such as microemulsions and nanoemulsions, gels, solids and liposomes.

Anti-aging effectiveness of retinol achieved by the composition is increased while side effects, such as skin redness/irritation, flaking, and peeling, caused by retinol are decreased with the addition of PDRN. PDRN helps fighting the potentially irritating side effects of retinol thanks to its soothing and healing properties. In particular, thanks to its anti-inflammatory properties, PDRN reduces redness and irritation of skin (anti-irritation effect). Further, thanks to its role as a skin repairing cellular growth stimulator, PDRN soothes skin flaking. Furthermore, thanks to its microcirculation improving effect, PDRN minimizes skin peeling.

Enhancement to Tolerability and Efficacy of 0.1% and 1.0% Retinol Creams by Addition of 1.0% PDRN.

Methods

Measurement of Cytokine Release in Cultured Human Skin Cells

Referring to FIG. 1, immortalized human keratinocytes HaCaT cells were cultured in 96-well plates and treated with 10 μM of all-trans retinol (Sigma-Aldrich, St. Louis, MO) and c-PDRN® obtained from (PharmaResearch, Seongnam-si, Gyeonggi-do, Korea) at the indicated concentrations. After incubation for 48 hours, cell supernatants were collected and the concentrations of cytokines such as MCP-I or IL-8 were measured by using a commercially available ELISA kits (R&D Systems, Minneapolis, MN) with manufacturer's suggested protocols. The levels of secreted cytokine were normalized against a standard dose-response curve.

Measurement of Expression and Phosphorylation of p38 Proteins in Cultured Human Skin Cells Referring to FIG. 1, altered signaling pathways in the retinol-treated HaCaT cells were investigated. The HaCaT cells were harvested 48 hours after treatment of retinol and c-PDRN at the indicated concentrations, and expression and phosphorylation levels of inflammation-related signaling mediator, p38 were determined using Western blot. Antibodies against p38 or phosphorylated p38 (p-p38) were purchased from Cell Signaling Technology (Danvers, MA).

Human Study of Anti-Irritant Efficacy Against Retinol-Induced Irritancy Using Patch Test Three subjects (age: 20~60) participated in this study. Subjects were asked not to take any influencing drugs such antihistamines and immunosuppressives, and not to use topical or systemic corticosteroids for at least 4 weeks before and during the test period. Pregnant or lactating women were excluded from this study. 0.5% c-PDRN was mixed with all-trans retinol (3000 IU or 0.09%) in 1.3-BG vehicle solution before the treatment and applied twice in Hill-Top chambers (Hill-Top, US) to the fore-arm of the subjects for 24 hours. Referring to Table 1, transepidermal water loss (TEWL) and Erythema Index were assessed at 30 min, 24 hour, 48 hour or 72 hour after removal of the chambers using Vapometer (Delfin Technology, Finland) and Mexameter MX18 (Courage+Khazaka GmbH, Germany), respectively. The accumulated data were calculated for evaluation of their anti-irritative effects of 0.5% c-PDRN on the retinol-induced inflammation.

TABLE 1

| Activities | Day 0 | Day 1 | Day 2 | Day 3 | Day 4 |
| --- | --- | --- | --- | --- | --- |
| Subject enrolment | ○ | | | | |
| Treatment with c-PDRN and retinol using Hill-Top chamber | ○ | ○ | | | |
| Evaluation of skin irritation | | ○ | ○ | ○ | ○ |
| Measurement of TEWL - Vapometer | ○ | ○ | ○ | ○ | ○ |
| Measurement of Erythema Index - Mexameter | ○ | ○ | ○ | ○ | ○ |

Comparative Study of Retinol Formulations with or without PDRN

In this study conducted by a board-certified dermatologist, 10 adult female subjects of Fitzpatrick skin type II who had passed initial medical and demographic screening were instructed in a skin care and treatment protocol developed to insure both uniformity and objectivity in acquisition and interpretation of results over a four-week study period. The subjects were given moisturizer and sunscreen which they were to use daily along with their regular cosmetics, and the subjects were not to vary their routine for the duration of the study. The subjects were further provided with sufficient quantities of the following two formulations:

Formulation A: a cosmetic cream with 0.1% retinol;
Formulation B: a cosmetic cream with 0.1% retinol plus 1.0% PDRN;

PDRN included in Formulations A and B was c-PDRN® obtained from PharmaResearch (Seongnam-si, Gyeonggi-do, Korea).

The subjects applied Formulation A to left side of face and Formulation B to right side of face.

Evaluations of Comparative Study

Digital images were acquired of each subject initially and at weeks 1, 2, 3, and 4, using a Canfield Scientific VISIA-CR system, evaluated by an expert who was blinded with respect to both the group assignment of the subject and the date of the image. Evaluations were of:

Erythema (redness);
Fine lines and wrinkles; and
Skin tone degradation.

Additionally, each subject completed a self-assessment questionnaire at the conclusion of the study.

Statistics of Comparative Study

Data for all measured parameters were analyzed for statistical significance by an independent statistician.

Results

Figure 2:
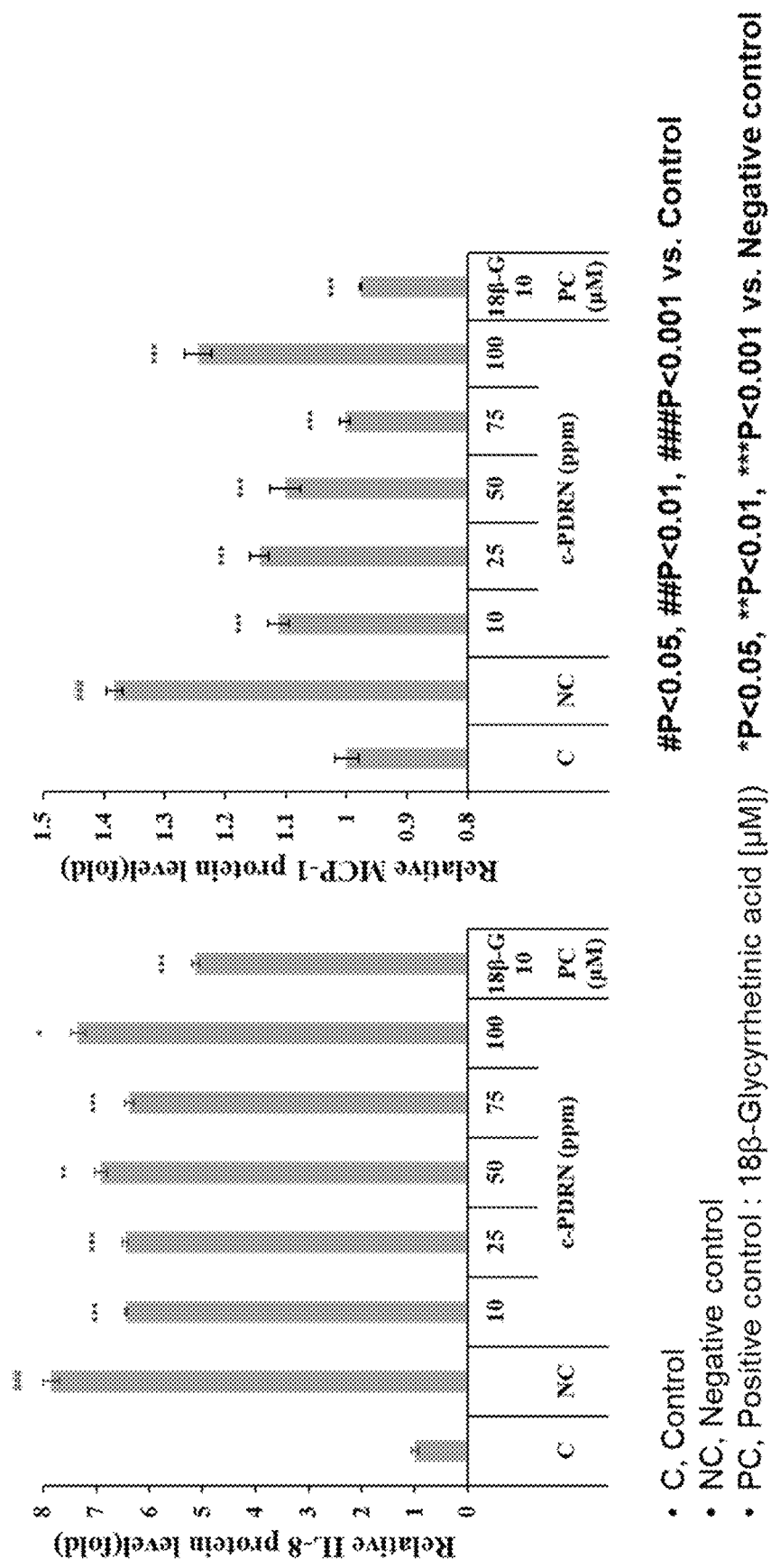
FIG. 2 shows graphs depicting anti-irritant activities of c-PDRN against retinol-induced irritation in accordance with various embodiments of the invention.

Inhibition of Retinol-Induced MCP-1/IL-8 Release in Immortalized Human Keratinocytes, HaCaT Cells by Treatment with c-PDRN c-PDRN is a hydrolyzed DNA fragment mixture extracted from the testes of adult salmon (*Oncorhynchus keta*, Salmonidae) The inhibitory effects of c-PDRN were evaluated on retinol-induced secretion of MCP-1 or IL-8 in cultured human keratinocytes, HaCaT cells by enzyme-linked immunosorbent assay (ELISA) to study IL-8, MCP-1 signaling pathway. The cultured HaCaT cells were treated with 10 μM all-trans retinol prior to c-PDRN treatment at the indicated concentrations. After incubation for 48 hours, the levels of secreted IL-8 or MCP-1 were measured and normalized against a standard IL-8 or MCP-1 dose-response curve. Data were shown as the means of three individual experiments with five wells per group. All-trans retinol induced increases in IL-8 and MCP-1 secretion by 8-fold and 1.4-fold, respectively. Efficacy range was c-PDRN 10 ppm~100 ppm or 0.001%-0.01%. As shown FIG. 2, c-PDRN inhibited retinol-induced MCP-1/IL-8 release in HaCaT cells at the concentrations of 10, 25, 50, or 75 ppm or 0.001, 0.0025, 0.005, or 0.0075%, i.e., the ratio of retinol:c-PDRN being 1:3.49, 1:8.74, 1:17, 1:26, respectively.

Figure 3:
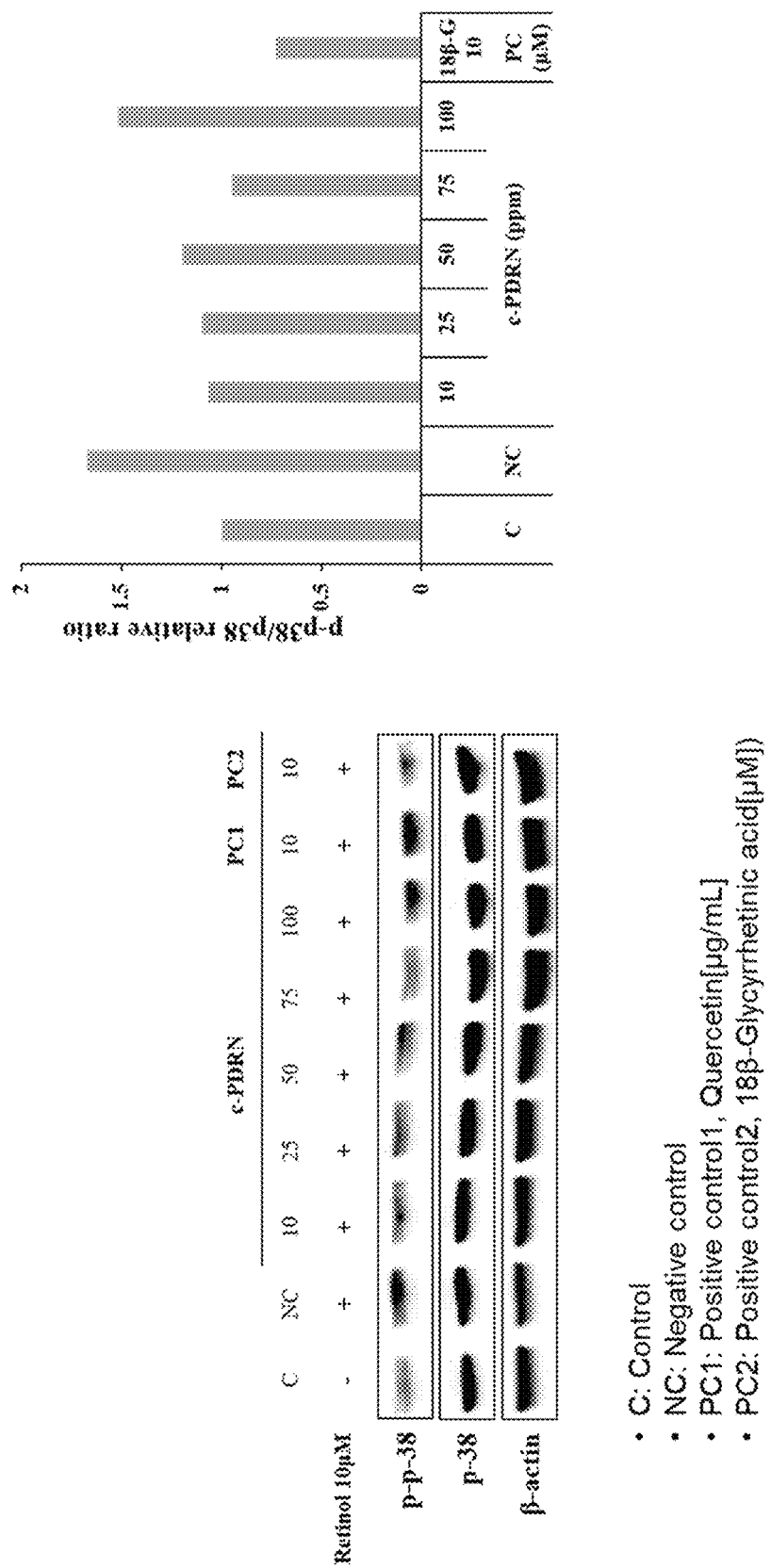
FIG. 3 shows a Western blot and a graph depicting anti-irritant activities of c-PDRN against retinol-induced irritation in accordance with various embodiments of the invention.

Inhibition of Retinol-Induced Phosphorylation of p38 in Immortalized Human Keratinocytes, HaCaT Cells by Treatment with c-PDRN The expression and phosphorylation levels of inflammation-related signaling mediator, p38 were evaluated after treatment with 10 μM all-trans retinol and c-PDRN at the indicated concentrations using Western blot to study p38 signaling pathway. As shown in FIG. 3, retinol induced phosphorylation of p38 protein (1.6-fold). c-PDRN inhibited retinol-induced phosphorylation of p38 at the concentrations of 10, 25, 50, or 75 ppm, as shown in FIG. 3, or 0.001, 0.0025, 0.005, or 0.0075%, i.e., the ratio of retinol:c-PDRN being 1:3.49, 1:8.74, 1:17, 1:26, respectively.

Figure 4:
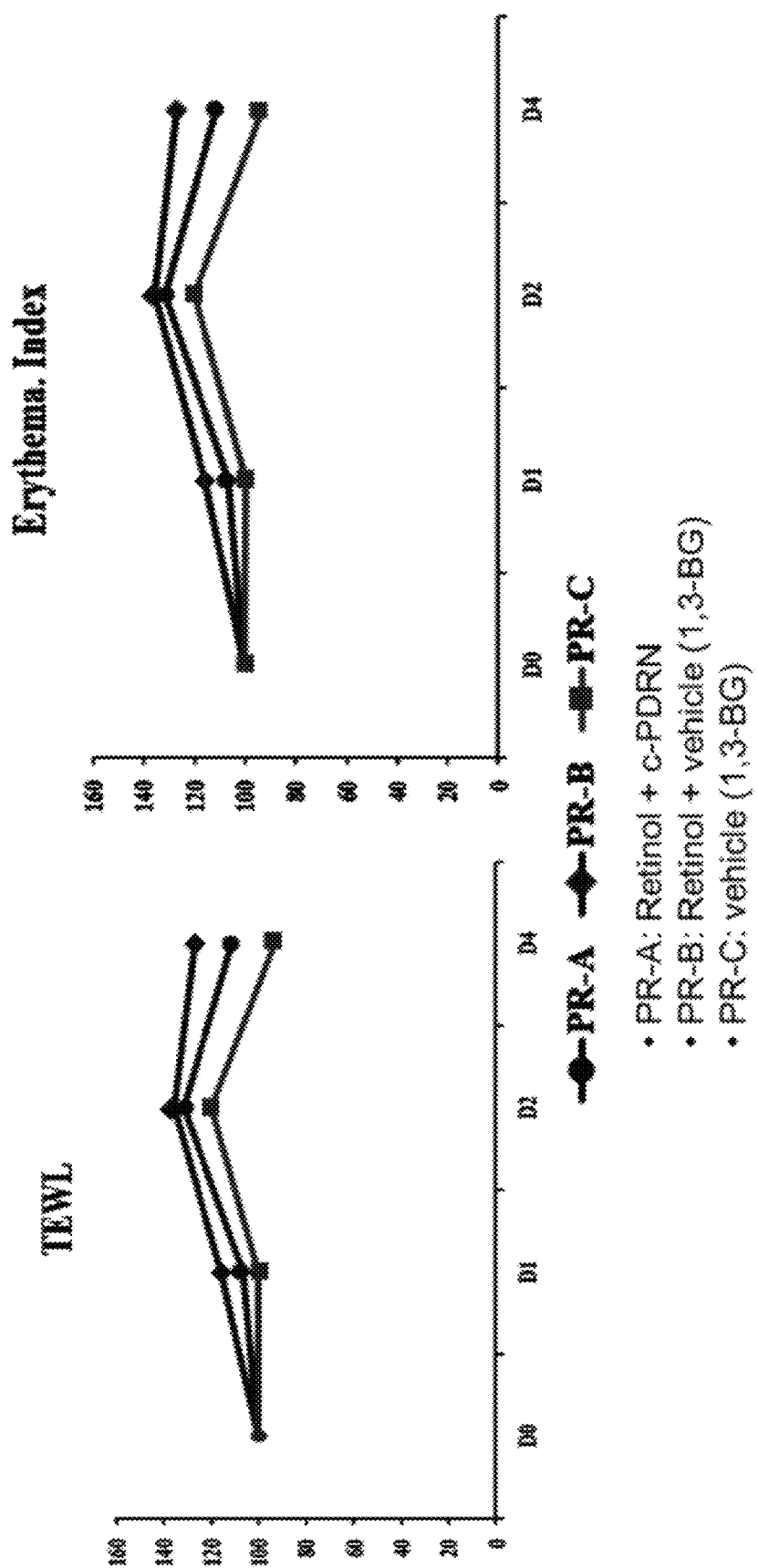
FIG. 4 shows graphs depicting anti-irritant activities of c-PDRN against retinol-induced irritation in human in accordance with various embodiments of the invention.

Attenuation of Retinol-Induced TEWL Increase and Erythema in Human Patch Test by Co-Treatment with c-PDRN Co-treatment with retinol and c-PDRN was performed on skin using Hill-Top chambers and measurements of TEWL (transepidermal water loss) and E.I (Erythema Index) were collected at days D1, D2, D3, and D4. As shown in FIG. 4, co-treatment with c-PDRN reduced the level of erythema in human patch test. Further, retinol-induced skin barrier disruption has been reported to induce TEWL increase 2-5 days after retinol treatment. As shown in FIG. 4, c-PDRN attenuated retinol-induced TEWL increase in human patch test.

Effects of Retinol Formulations with c-PDRN on Skin

The average age of 10 subjects in this study was 55 years, ranging from 45 to 70. The digital images were evaluated for erythema (redness), fine lines and wrinkles, and skin tone degradation.

Figure 5:
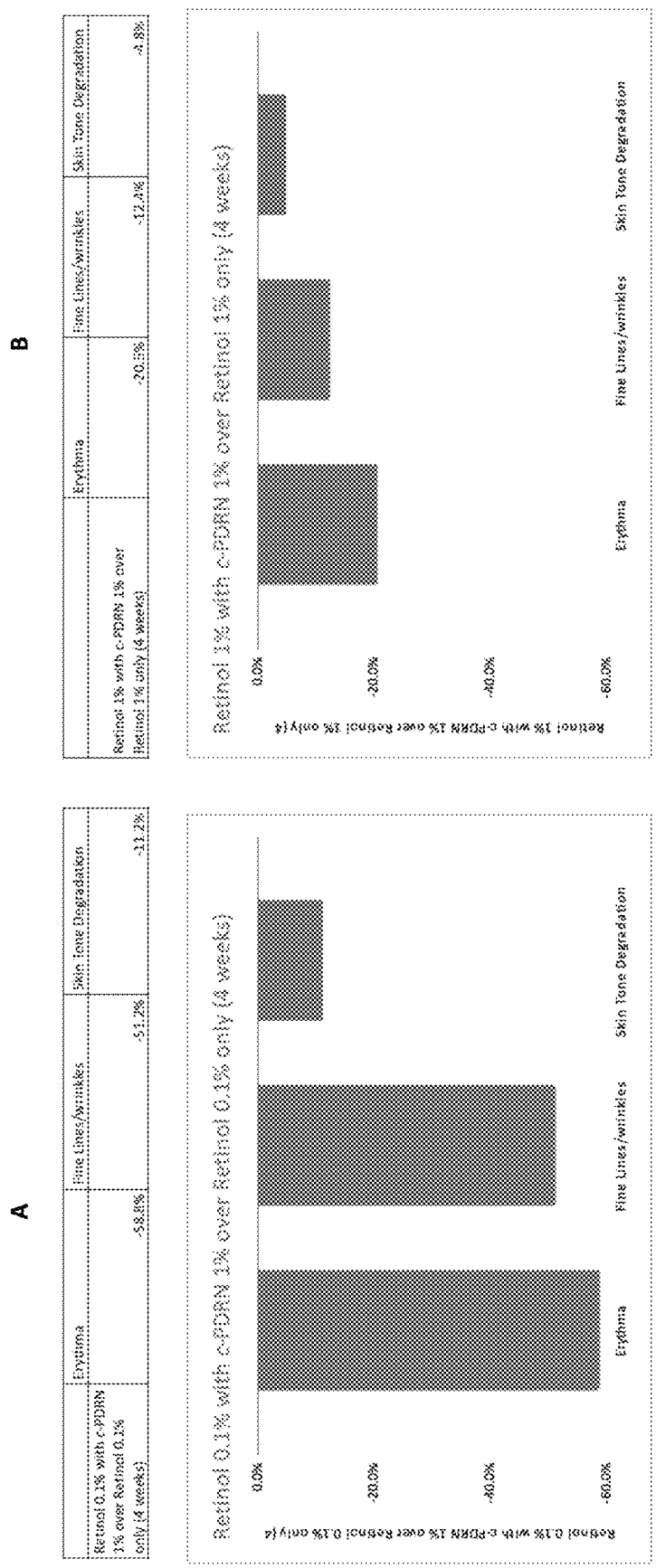
FIG. 5 shows graphs depicting the calculated average results of the four-week assessments performed on facial skin of subjects with compositions in accordance with various embodiments of the invention.

As shown in FIG. 5, the graph depicts the calculated average results of the four-week assessments performed by the expert dermatologist. In particular, the graph of FIG. 5 shows that the marginal efficacy of retinol alone, at the 0.1% level, is markedly improved with respect to all appearance categories evaluated, by supplementation with 1% PDRN; almost 60% less erythema, 50% fewer fine lines, and 11% less skin tone degradation.

Conclusion

The addition of c-PDRN to the retinol-based skin care formulation has a synergistic effect, enhancing both the efficacy and the tolerability after four weeks of use. That is, the addition of PDRN clearly boosts reduction of erythema, fine lines and wrinkles, and skin tone degradation achieved by retinol. This synergy is particularly vital when a low dose, for example 0.1%, of retinol is used, as shown in FIG. 5.

Methods of Skin Care Treatment

In various embodiments, the present invention provides a method for treating a subject's skin, including skin on any portion of the subject's body. In certain embodiments, the method includes applying a formulation described herein to the subject's skin. In some embodiments, the method includes applying a formulation described herein to a subject's face.

Facial/Neck Wrinkles

Figure 6:
FIG. 6 illustrates effects of a composition, in accordance with various embodiments of the invention, on facial skin of a subject.

The composition comprising 0.1% retinol and 0.5% c-PDRN was applied to various skin parts of a subject's face for 4 weeks, once a day at night time, and the appearance of skin was observed 4 weeks after the initial application of the composition. Referring to FIG. 6, fine lines were no longer noticeable and deep lines were visibly diminished for a smoother, younger appearance after 4 week use of the composition. Referring to the bottom panel in FIG. 6, the appearance of sagging neck skin was noticeably improved with greater firmness and fewer visible wrinkles were present after 4 week use of the composition. After 4 week use of the composition, the subject indicated that wrinkles looked much smoother, cheeks felt much smoother, the deep wrinkles improved, the "smoker's lines" above lips looked more relaxed, the lines on the side of mouth were less noticeable, and lips were much smoother.

Pigmentation and Scar Reduction

Figure 7:
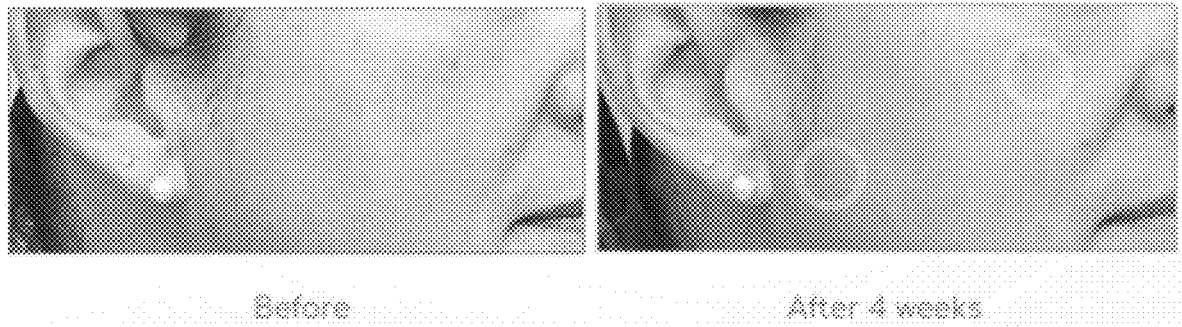
FIG. 7 illustrates effects of a composition, in accordance with various embodiments of the invention, on acne scars of a subject.

The composition comprising 0.1% retinol and 0.5% c-PDRN was applied to old acne scars of a subject's face for 4 weeks, once a day at night time, and the appearance of skin was observed 4 weeks after the initial application of the composition. Referring to FIG. 7, noticeable fading of age spots and dark pigmentation from old acne scars was visible after 4 week use of the composition, resulting in a more even complexion. After 4 week use of the composition, the subject indicated that her face felt firmer, dewier, and more lifted.

Crow's Feet

Figure 8:
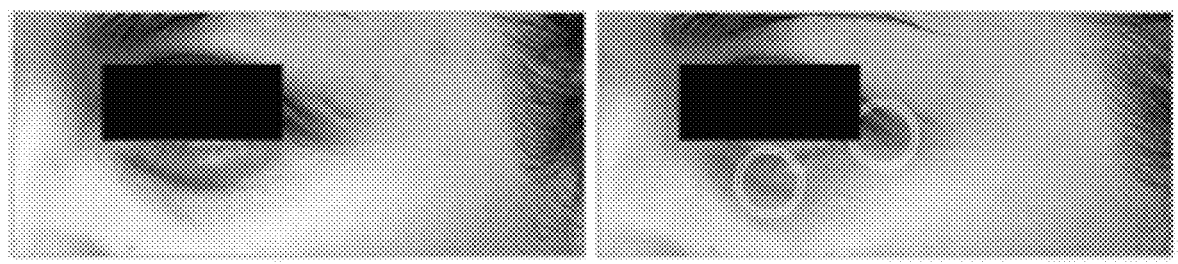
FIG. 8 illustrates effects of a composition, in accordance with various embodiments of the invention, on wrinkles around an eye area of a subject.

The composition comprising 0.1% retinol and 0.5% c-PDRN was applied to crow's feet or fine lines around the eye area of a subject's face for 4 weeks, once a day at night time, and the appearance of skin was observed 4 weeks after the initial application of the composition. Referring to FIG. 8, dramatic improvement in the appearance of wrinkles around the eye area was visible after 4 week use of the composition.

Eye Bags

Figure 9:
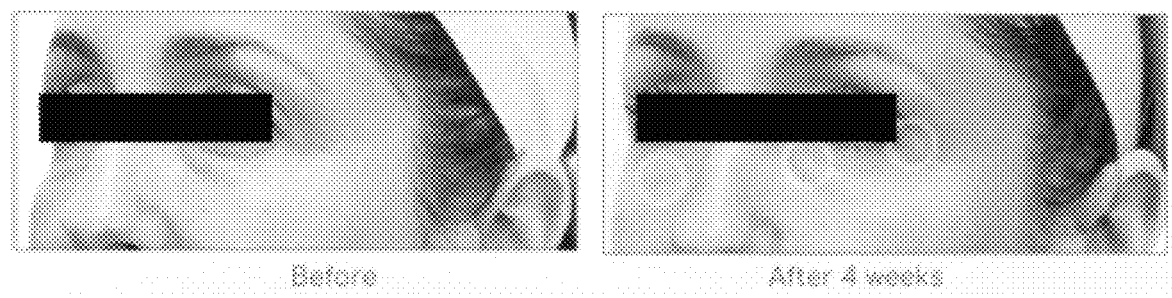
FIG. 9 illustrates effects of a composition, in accordance with various embodiments of the invention, on wrinkles around an eye area of a subject.

The composition comprising 0.1% retinol and 0.5% c-PDRN was applied to eye bags or mild swelling or puffiness under the eyes of a subject's face for 4 weeks, once a day at night time, and the appearance of skin was observed 4 weeks after the initial application of the composition. Referring to FIG. 9, dramatic improvement in the appearance of wrinkles around the eye area was visible after 4 week use of the composition. After 4 week use of the composition, the subject indicated that she noticed a difference after just 1 week use of the composition and the skin felt smoother and healthier.

Eye Wrinkles

Figure 10:
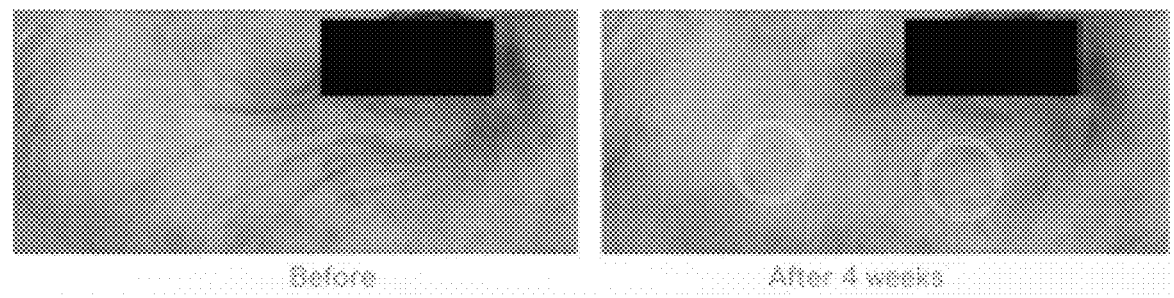
FIG. 10 illustrates effects of a composition, in accordance with various embodiments of the invention, on wrinkles around an eye area of a subject.

The composition comprising 0.1% retinol and 0.5% c-PDRN was applied to wrinkles around the eyes of a subject's face for 4 weeks, once a day at night time, and the appearance of skin was observed 4 weeks after the initial application of the composition. Referring to FIG. 10, dramatic improvement in the appearance of wrinkles around the eye area was visible after 4 week use of the composition. After 4 week use of the composition, the subject indicated that the skin is smoother and the sun spots are definitely lighter.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. A facial treatment composition comprising:
   an excipient base in the range of about 94.00-about 99.98% w/w;
   vitamin A1-alcohol (retinol); and
   polydeoxyribonucleotide (PDRN),
   wherein a weight ratio of retinol to PDRN in the composition is in the range of 1:5 to 1:10, an amount of PDRN being greater than an amount of retinol such that PDRN is effective as an anti-irritant in response to skin irritations causable by retinol applied to skin of a subject, and
   wherein facial treatment includes treatment of a facial area of the subject including a neck, cheeks, areas around lips, and/or areas around eyes.

2. The facial treatment composition of claim 1, wherein:
   the amount of retinol in the facial treatment composition is in the range of 0.01-1.00% w/w; and
   the amount of PDRN in the facial treatment composition is in the range of 0.01-5.00% w/w.

3. The facial treatment composition of claim 2, wherein the amount of retinol is about 0.1% w/w.

4. The facial treatment composition of claim 2, wherein the amount of retinol is about 1% w/w.

5. The facial treatment composition of claim 1, wherein the composition is a topical composition.

6. The facial treatment composition of claim 5, wherein the facial treatment composition is a cosmetic, skin care, or anti-aging composition.

7. A method for treating a sign of skin aging, the method comprising topically applying the composition of claim 1 to facial skin of a subject in need of treatment for skin aging, the facial skin including the neck, cheeks, areas around the lips, and/or areas around the eyes.

8. The method of claim 7, wherein the treating the sign of skin aging comprises reducing fine lines and wrinkles on the facial skin.

9. The method of claim 7, wherein the composition is applied to the facial skin 1-3 times a day.

10. The method of claim 7, wherein the composition is applied to the facial skin every 6-8 hours.

11. The method of claim 7, wherein the facial skin further includes fine lines, deep lines, or wrinkles on the cheeks and/or around the eyes, lines on a side of the mouth, smoker's lines above the lips, crow's feet or fine lines around the eyes, and/or eye bags or mild swelling or puffiness under the eyes.

12. The method of claim 7, wherein the composition is topically applied to acne scars on the facial skin such that visibility of the acne scars disappears or is reduced.

13. The method of claim 7, wherein:
an amount of retinol in the composition is in the range of 0.01-1.00% w/w;
an amount of PDRN in the composition is in the range of 0.01-5.00% w/w; and
the amount of PDRN is effective to treat, reduce or prevent skin irritations causable by retinol applied to facial skin of a subject.

14. The method of claim 13, wherein the amount of retinol in the composition is about 0.1% w/w.

15. The method of claim 13, wherein the amount of retinol in the composition is about 1% w/w.

* * * * *